(12) United States Patent
Dufour et al.

(10) Patent No.: US 11,120,564 B2
(45) Date of Patent: Sep. 14, 2021

(54) MEDICAL IMAGING APPARATUS AND MEDICAL IMAGING METHOD FOR INSPECTING A VOLUME OF A SUBJECT

(71) Applicant: KONINKLIJKE PHILIPS N.V., Eindhoven (NL)

(72) Inventors: Cecile Dufour, Suresnes (FR); Stephane Allaire, Suresnes (FR); Thomas Tang, Markham (CA); Gary Cheng-How Ng, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 217 days.

(21) Appl. No.: 16/063,811

(22) PCT Filed: Dec. 20, 2016

(86) PCT No.: PCT/IB2016/057808
§ 371 (c)(1),
(2) Date: Jun. 19, 2018

(87) PCT Pub. No.: WO2017/109685
PCT Pub. Date: Jun. 29, 2017

(65) Prior Publication Data
US 2020/0273184 A1   Aug. 27, 2020

Related U.S. Application Data

(60) Provisional application No. 62/270,868, filed on Dec. 22, 2015.

(51) Int. Cl.
*G06T 7/33* (2017.01)
*G06T 7/12* (2017.01)
(Continued)

(52) U.S. Cl.
CPC .............. *G06T 7/33* (2017.01); *A61B 6/032* (2013.01); *A61B 6/5247* (2013.01);
(Continued)

(58) Field of Classification Search
CPC .... G06T 7/33; G06T 7/12; G06T 7/70; G06T 5/50; G06T 7/0012; G06T 7/20;
(Continued)

(56) References Cited

U.S. PATENT DOCUMENTS 6,447,450 B1 * 9/2002 Olstad .................. A61B 5/0456
600/437
2003/0233039 A1   12/2003 Shao et al.
(Continued)

FOREIGN PATENT DOCUMENTS

WO   2004103181 A1   12/2004
WO   2011015801 A1    2/2011

*Primary Examiner* — Jianxun Yang (57) ABSTRACT

A medical imaging apparatus (10) for inspecting a volume of a subject (12) is disclosed. The medical imaging apparatus comprises an ultrasound acquisition unit (14) including an ultrasound probe for acquiring ultrasound image data of the subject, an image interface (20) for receiving medical image data of the subject, a position determining unit (30) for determining a position of the ultrasound probe. An alignment unit is provided for aligning the ultrasound image data and the medical image data based on anatomical features (32) of the subject and the detected position of the ultrasound probe and for adapting the alignment of the ultrasound image data and the medical image data based on a motion model. An image processing unit (18) is provided for processing the ultrasound image data and the medical image data to fuse the ultrasound image data and the medical image data based on the alignment to combined image data.

13 Claims, 5 Drawing Sheets

(51) Int. Cl.
    *G06T 7/70*     (2017.01)
    *A61B 6/03*     (2006.01)
    *A61B 6/00*     (2006.01)
    *A61B 8/00*     (2006.01)
    *A61B 8/08*     (2006.01)
    *G06T 5/50*     (2006.01)
    *G06T 7/00*     (2017.01)
    *G06T 7/20*     (2017.01)
    *G06T 7/13*     (2017.01)

(52) U.S. Cl.
    CPC ............ *A61B 8/4254* (2013.01); *A61B 8/463* (2013.01); *A61B 8/483* (2013.01); *A61B 8/5261* (2013.01); *A61B 8/5292* (2013.01); *G06T 5/50* (2013.01); *G06T 7/0012* (2013.01); *G06T 7/12* (2017.01); *G06T 7/20* (2013.01); *G06T 7/70* (2017.01); *G06T 7/13* (2017.01); *G06T 2200/24* (2013.01); *G06T 2207/10136* (2013.01); *G06T 2207/20221* (2013.01); *G06T 2207/30004* (2013.01)

(58) Field of Classification Search
    CPC .................. G06T 7/13; G06T 2200/24; G06T 2207/10136; G06T 2207/20221; G06T 2207/30004; G06T 7/35; G06T 15/08; G06K 2209/05; A61B 6/032; A61B 6/5247; A61B 8/4254; A61B 8/463; A61B 8/483; A61B 8/5261; A61B 8/5292; A61B 8/06; A61B 5/0456
    See application file for complete search history.

(56) References Cited

U.S. PATENT DOCUMENTS

| | | |
|---|---|---|
| 2008/0226149 A1 | 9/2008 | Wischmann et al. |
| 2008/0283771 A1 | 11/2008 | Li |
| 2009/0303252 A1 | 12/2009 | Hyun et al. |
| 2010/0310140 A1* | 12/2010 | Schneider ................ G06T 7/35 |
| | | 382/130 |
| 2011/0028843 A1 | 2/2011 | Hyun et al. |
| 2012/0253170 A1 | 10/2012 | Kim et al. |
| 2013/0039555 A1 | 2/2013 | Xu et al. |
| 2014/0193053 A1* | 7/2014 | Kadoury ................ G06T 15/08 |
| | | 382/131 |
| 2014/0235998 A1 | 8/2014 | Kim et al. |

* cited by examiner

FIG.7

MEDICAL IMAGING APPARATUS AND MEDICAL IMAGING METHOD FOR INSPECTING A VOLUME OF A SUBJECT

This application is the U.S. National Phase application under 35 U.S.C. § 371 of International Application No. PCT/IB2016/057808 filed on Dec. 20, 2016, which claims the benefit of Provisional Application Ser. No. 62/270,868, filed Dec. 22, 2015. These applications are hereby incorporated by reference herein.

FIELD OF THE INVENTION

The present invention relates to a medical imaging apparatus for inspecting a volume of the subject, in particular a medical imaging apparatus combining ultrasound image data and medical image data of a subject. The present invention further relates to a medical imaging apparatus for inspecting a volume of a subject, in particular a method for combining ultrasound image data and medical image data of the subject.

BACKGROUND OF THE INVENTION

In the field of medical imaging systems it is generally known to fuse live ultrasound images of a patient with pre-operative volume images like computer tomography images of the same patient in order to improve the diagnostic possibilities. These systems usually spatially align the different image data by means of a calibrated electromagnetic tracking system, wherein the tracking system allows to maintain the spatial synchronization between the ultrasound image data and the pre-operative volume image data. A corresponding medical imaging system is e.g. known from US 2011/028843 A1.

The alignment of the ultrasound image data and the pre-operative image data is based on a spatial calibration of the tracking system and a rigid transformation between the ultrasound image data coordinates and the pre-operative volume image coordinates. The calibration of the different image data coordinates is therefore more accurate if the pre-operative image scan is performed shortly before the ultrasound scan and if the calibration position is close to the position of the image data to be aligned.

Even if the spatial calibration of the tracking system is highly accurate, the alignment of the different image data shows misalignments due to cardiac and/or respiratory motions of the patient.

SUMMARY OF THE INVENTION

It is therefore an object of the present invention to provide a medical imaging apparatus for inspecting a volume of a subject providing an improved alignment of different image data even if the volume to be inspected is in motion.

It is a further object of the present invention to provide a corresponding medical imaging method for inspecting a volume of a subject.

According to one aspect of the present invention, a medical imaging apparatus for inspecting a volume of a subject is provided comprising:

an ultrasound acquisition unit including an ultrasound probe for acquiring a plurality of ultrasound image data of the subject,
an image interface for receiving medical image data of the subject,
a position determining unit for determining a position of the ultrasound probe,
an image processing unit arranged to determine a motion model of the volume based on the plurality ultrasound image data and to align the ultrasound image data and the medical image data based on the motion model, wherein the image processing unit comprises
an fusion unit for processing the ultrasound image data and the medical image data to fuse the ultrasound image data and the medical image data based on the alignment to combined image data.

According to another aspect of the present invention, a medical imaging method for inspecting a volume of a subject is provided comprising the steps of:

acquiring a plurality of ultrasound image data ultrasound image data of the subject by an ultrasound acquisition unit including an ultrasound probe,
receiving medical image data of the subject via an image interface,
determining a position of the ultrasound probe,
determining a motion model of the volume based on the plurality ultrasound image data,
aligning the ultrasound image data and the medical image data,
adapting the alignment of the ultrasound image data and the medical image data based on the motion model, and
processing the ultrasound image data and the medical image data to fuse the ultrasound image data and the medical image data based on the alignment to combined image data.

Preferred embodiments of the invention are defined in the dependent claims. It shall be understood that the claimed method has similar and/or identical preferred embodiments as the claimed device and as defined in the dependent claims.

The present invention is based on the idea to align the ultrasound image data and the medical image data, which is a pre-operative volume image data of the same patient preferably on the basis of a position of the ultrasound probe and anatomical features of the subject. The ultrasound image data and the medical image data are aligned and the alignment is adapted if a misalignment occurs due to a motion of the anatomical features to be imaged based on a determined motion model. On the basis of the motion model, the motion state of the anatomical features to be imaged can be estimated and an alignment of the image data can be performed continuously. Hence, a precise alignment of the different image data can be achieved and the alignment of the image data can be maintained continuously even if anatomical features like organs of the patient are in motion e.g. by respiration.

In a preferred embodiment, the image processing unit is adapted to determine corresponding anatomical features in the ultrasound data and the medical image data and to align the ultrasound data and the medical image data based on the corresponding anatomical features. This is a possibility to achieve a precise alignment of the ultrasound image data and the medical image data.

In a preferred embodiment, the image processing unit is adapted to align the ultrasound data and the medical image data based on a distance between the determined corresponding anatomical features. This is a possibility to align the ultrasound data and the medical image data with low technical effort.

In a preferred embodiment, the image processing unit comprises a segmentation unit for providing segmentation data of anatomical features of the subject, wherein the image processing unit further comprises an alignment unit adapted to align the ultrasound image data and the medical image data based on the segmentation data. This is a possibility to precisely align the ultrasound image data and the medical image data based on the image data.

In a preferred embodiment, the image processing unit is adapted to determine a motion state of the anatomical features on the basis of the motion model, and wherein the alignment unit is configured to adapt the alignment of the ultrasound image data and the medical image data on the basis of the determined motion state and the motion model. This is a possibility to align the ultrasound image data and the medical image data precisely corresponding to a motion of the anatomical features.

In a preferred embodiment, the image processing unit is adapted to determine a plurality of different image planes in the medical image data, based on the detected position of the ultrasound probe. This is a possibility to provide an alignment with the ultrasound image data with low technical effort.

In a preferred embodiment, the ultrasound probe is adapted to acquire two-dimensional ultrasound image data, wherein the alignment unit is adapted to align the two-dimensional ultrasound image data to one of the different image planes of the medical image data based on the motion model. This is a possibility to align the two-dimensional ultrasound image data and the image planes of the medical image data precisely based on the motion model.

In a preferred embodiment, the different image planes are disposed in parallel to each other. This is a possibility to align the two-dimensional ultrasound image data and the image planes with low technical effort.

In a further preferred embodiment, the different image planes are disposed in parallel to a calibrated image plane of the medical image data. This is a further possibility to reduce the technical effort for aligning the ultrasound image data and the medical image data.

In an alternative embodiment, the ultrasound probe is adapted to acquire three-dimensional ultrasound image data of the subject and wherein the alignment unit is adapted to align an image plane of the three-dimensional ultrasound image data to one of the different image planes of the medical image data based on the motion model. This is a possibility to align three-dimensional ultrasound image data with three-dimensional medical image data precisely based on the motion model.

In a preferred embodiment, the alignment unit is further adapted to select one of the different image planes of the medical image data for alignment with the ultrasound image data on the basis of corresponding anatomical features identified in the ultrasound image data and the medical image data. This is a possibility to further improve the preciseness of the alignment of the ultrasound image data and the medical image data.

In a further preferred embodiment, the alignment unit is adapted to select one of the different image planes of the medical image data for alignment with the ultrasound image data further on the basis of a probability algorithm. This is a possibility to improve the robustness of the selection and the alignment of the ultrasound image data and the medical image data. In a preferred embodiment, the probability algorithm is a Viterbi algorithm.

In a preferred embodiment, the motion model is determined based on the position of the ultrasound probe determined by the position determining unit. This is a possibility to utilize different motion models for different anatomical features to be imaged and to improve the preciseness of the alignment.

In a preferred embodiment, the motion model includes a cranio-caudal translation model. This is a possibility to estimate the motion of the anatomical features of the subject precisely dependent on the detected ultrasound probe position.

In a preferred embodiment, the alignment unit is adapted to align the ultrasound image data and the medical image data based on anatomical features of the subject and the detected position of the ultrasound probe.

As mentioned above the alignment of the ultrasound image data and the medical image data can be significantly improved since the motion of the anatomical features of the subject are estimated based on the motion model and based on the correlation of the ultrasound image data and the medical image data. In particular a motion of anatomical features of the subject can be determined based on the ultrasound data so that e.g. a breathing motion of the subject can be considered and the alignment of the two different image data can be correspondingly adapted. Hence, a precise alignment of the ultrasound image data and the medical image data can be achieved even if the anatomical features of the subject are in motion.

BRIEF DESCRIPTION OF THE DRAWINGS

These and other aspects of the invention will be apparent from and elucidated with reference to the embodiment(s) described hereinafter. In the following drawings

FIGS. 2a, b show an ultrasound image and a computer tomography image to be fused by the medical imaging apparatus to combined medical image data;

DETAILED DESCRIPTION OF THE INVENTION

Figure 1:
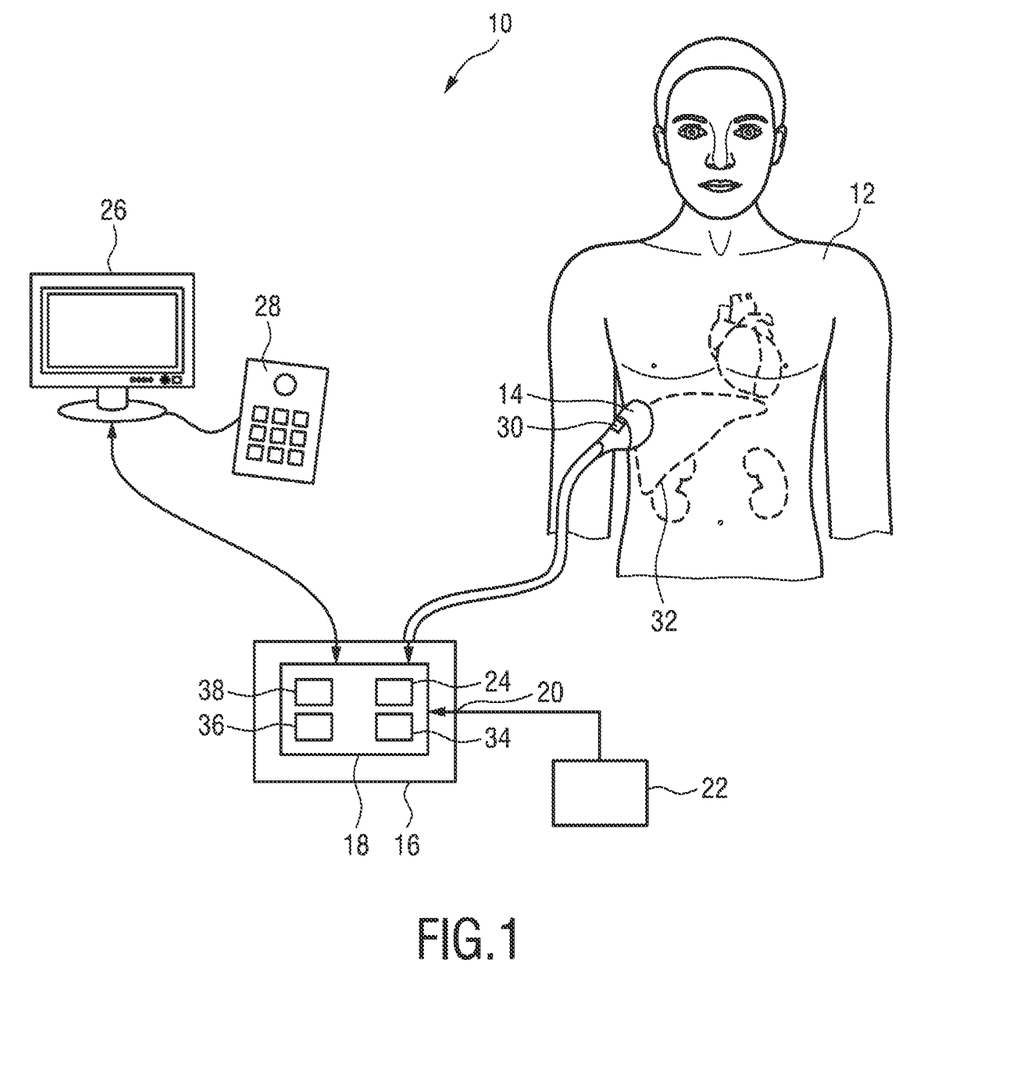
FIG. 1 shows a schematic representation of a medical imaging apparatus for inspecting a volume of a subject.

FIG. 1 shows a schematic illustration of a medical imaging apparatus generally denoted by 10. The medical imaging apparatus 10 is applied to inspect a volume of an anatomical site, in particular an anatomical site of a patient 12. The medical imaging apparatus 10 comprises an ultrasound probe 14 having at least one transducer array including a multitude of transducer elements for transmitting and receiving ultrasound waves. The transducer elements are arranged in a string of elements or as a 2D-array.

The medical imaging apparatus 10 comprises in general a control unit 16 connected to the ultrasound probe 14 for controlling the acquisition of ultrasound data and in particular for steering and/or beam forming purposes of the ultrasound waves. The control unit 16 comprises an image processing unit 18 connected to the ultrasound probe 14 for evaluating the ultrasound data received from the ultrasound probe 14 and for fusing or combining or correlating the ultrasound image data with pre-operative images of the patient 12. The image processing unit 18 comprises an image interface 20 for receiving the pre-operative 3D-medical image data from a database 22 or an external analysis and imaging apparatus 22. The pre-operative image data is preferably computer tomography image data (CT), magnetic resonance tomography image data (MRT), or Cone Beam CT image data or pre-operative 3D-ultrasound image data. The image processing unit 18 comprises a fusion unit 24 for combining the ultrasound images received from the ultrasound probe 14 and the pre-operative medical image data of the patient 12 received from the database 22 or the external analysis and imaging apparatus 22.

The medical imaging apparatus 10 further comprises a display unit 26 for displaying image data received from the fusion unit 18. The display unit 26 receives the image data in general from the image processing unit 18 and is adapted to display the ultrasound image data and the medical image data as combined image data e.g. as overlay images. The medical imaging apparatus 10 further comprises an input device 28 which may be connected to the display unit 26 or to the control unit 16 in order to control the image acquisition. The input device 28 may comprise a keyboard or a mouse or the like or may be formed as a touchscreen of the display unit 26 to control the medical imaging apparatus 10 in general.

The medical imaging apparatus 10 further comprises a position determining unit 30 attached to the ultrasound probe 14 for determining a position of the ultrasound probe 14. The position determining unit 30 determines a position of the ultrasound probe 14 in use attached to the body of the patient 12 e.g. by means of electromagnetic tracking. The position of the ultrasound probe 14 is utilized to correlate the ultrasound image data acquired by the ultrasound probe 14 and the medical image data received via the image interface 20 as pre-operative medical image data of the patient 12. The ultrasound probe 14 is in use adapted to provide ultrasound image data from anatomical features 32 of the patient 12 which are schematically shown in FIG. 1, wherein a preferred anatomical feature of the patient 12 is the liver to be scanned by the ultrasound probe 14.

The image processing unit 18 comprises a calibration unit 34 for calibrating the position determining unit 30 with respect to the pre-operative medical image data received via the image interface 20 with the respective ultrasound image data captured by the ultrasound probe 14 at an initial calibration position. The image processing unit 18 may further comprise a segmentation unit 36 for segmenting the ultrasound image data and the medical image data and for providing corresponding segmentation data. The segmentation unit 36 provides the segmentation data based on pattern and/or edge detection within the ultrasound image data and the medical image data. The registration unit 24 registers or correlates the ultrasound image data and the pre-operative medical image data preferably on the basis of the segmentation data received from the segmentation unit 36.

The image processing unit 18 further comprises a motion model 38 of the anatomical features 32 of the subject 12 which describes a motion of the anatomical features 32 within the patient's body based on the detected position of the ultrasound probe 14 and the respective viewing direction. The motion model 38 provides an indication of a motion or a movement of the anatomical feature 32 within the patient's body so that the alignment of the ultrasound image data captured by the ultrasound probe 14 can be precisely correlated to the corresponding pre-operative medical image data of the patient 12 even if the anatomical feature 32 is in motion due to vital movements of the patient 12 like respiration. Further, the alignment of the ultrasound image data and the medical image data can be adapted or corrected based on the motion model and an estimated motion of the anatomical features. The motion model preferably includes a cranio-caudal translation model.

During the ultrasound scan, the registration unit 24 fuses the ultrasound image data acquired by the ultrasound probe 14 with the medical image data of the same position of the anatomical feature 32. The alignment of the ultrasound image data and the pre-operative medical image data is achieved by correlation of anatomical features detected in the ultrasound image data and the pre-operative medical image data. The ultrasound image data and the pre-operative medical image data of the subject 12 can be aligned based on the motion model of the anatomical feature 32 e.g. due to the respiration of the subject 12. Hence, the fusion of the two different image data can be improved.

In a first step, the motion model 38 is selected based on the determined position of the ultrasound probe 14 and a plurality of image planes in the pre-operative medical image data are determined. In a following step the captured ultrasound image data, the respective position of the ultrasound probe 14 are correlated to each other. One of the image planes in the pre-operative medical image data is selected as a calibrated position, which fits to the captured two-dimensional ultrasound image data, e.g. based on feature detection and/or segmentation data in the ultrasound image data and the pre-operative medical image data. Based on the motion model 38 and the correspondingly expected movement of the anatomical feature 32, in this particular case the liver 32 with respect to the ultrasound probe 14 and the selected image plane, a different slice of the pre-operative medical image data is selected and registered or fused with the currently captured ultrasound image data. The correct fusion of the ultrasound image data and the corresponding pre-operative medical image data at the calibration position can be maintained or a misalignment can be corrected based on the motion model 38. Hence, a movement e.g. due to respiration of the anatomical features 32, i.e. the organs of the subject 12 can be considered so that in any case a correct fusion or registration of the different image data can be achieved.

Figure 2:
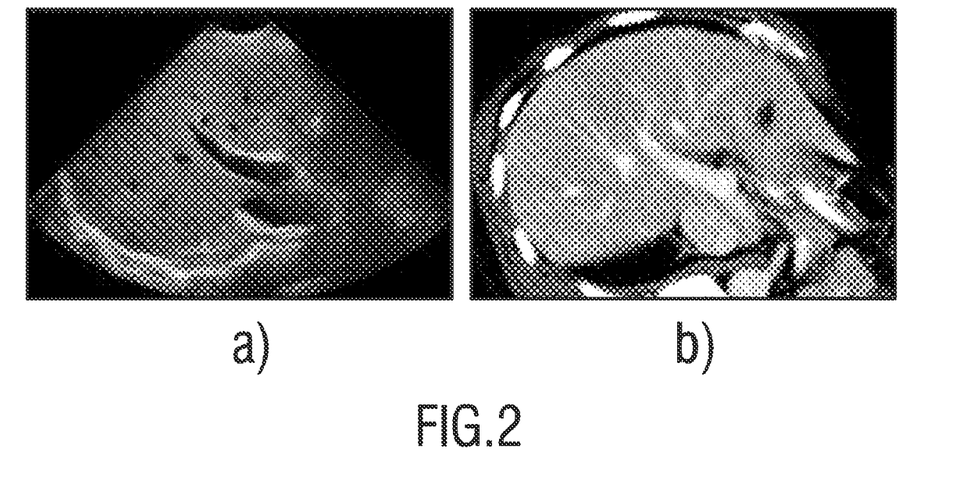

In FIG. 2a, b ultrasound and computer tomography images are shown for calibration of the medical imaging apparatus 10. The images show the liver 32 as the anatomical feature of the subject 12, wherein FIG. 2a shows the liver 32 captured by the ultrasound probe 14 and FIG. 2b shows a corresponding image plane of the computer tomography image data of the liver 32. The positions of the vessels of the liver 32 correspond to each other so that a good alignment can be achieved. The calibration can be performed on the basis of pattern detection and/or edge detection in the different image data and on the basis of segmentation data of the respective image data so that a precise alignment and a precise calibration of the medical imaging apparatus 10 can be achieved.

Figure 3:
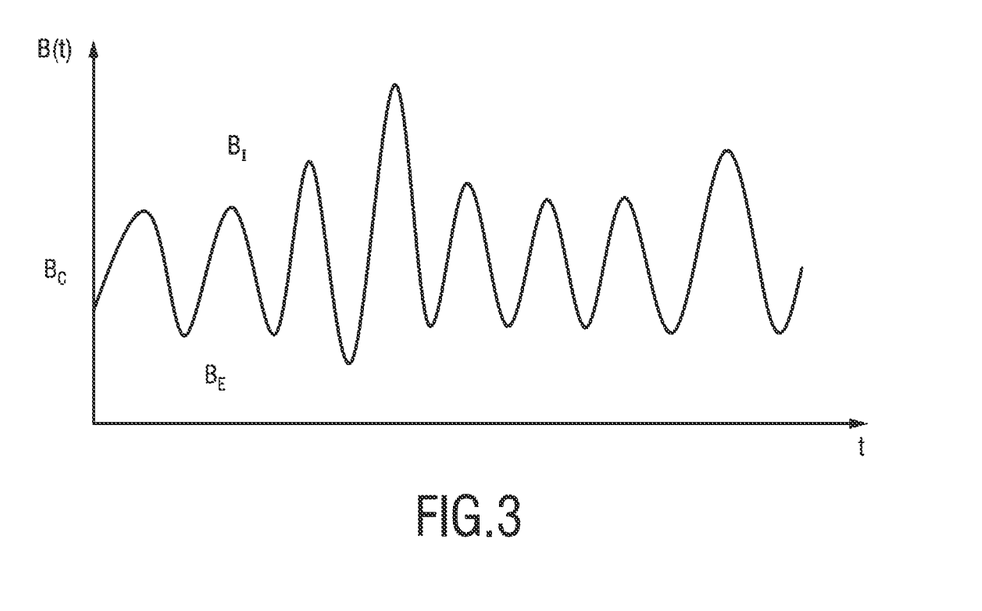
FIG. 3 shows a timing diagram of the respiration of the subject during medical scan.

FIG. 3 shows a timing diagram of a respiration function B(t) of the subject 12. In FIG. 3, a calibration position $B_C$ or an initial position of the ultrasound probe 14 is determined, wherein the respiration function B(t) as a motion state of the anatomical features of the subject 12 alternates around the calibration position $B_C$. The peaks above the calibration position $B_C$ correspond to an inhalation $B_I$ of the subject and the lower peaks correspond to an exhalation $B_E$ of the subject 12.

Due to the respiration of the subject 12, the inner organs 32 of the subject 12 move in a cranio caudal direction with respect to the ultrasound probe 14 even if the ultrasound probe 14 is held fixedly with respect to the skin of the subject 12 as described in detail below.

FIGS. 4*a-f* show schematic illustrations of the subject 12 including the anatomical features 32, which move in a cranio caudal direction during a respiration cycle of the subject 12. The ultrasound probe 14 is schematically shown inspecting the liver 32 as the anatomical feature 32, wherein the ultrasound probe 14 is in a fixed position with respect to the skin of the subject 12. In FIGS. 5*a-f,* the corresponding ultrasound images and the corresponding pre-operative computer tomography images for the respective respiration cycle shown in FIGS. 4*a-f* are shown.

Figure 4:
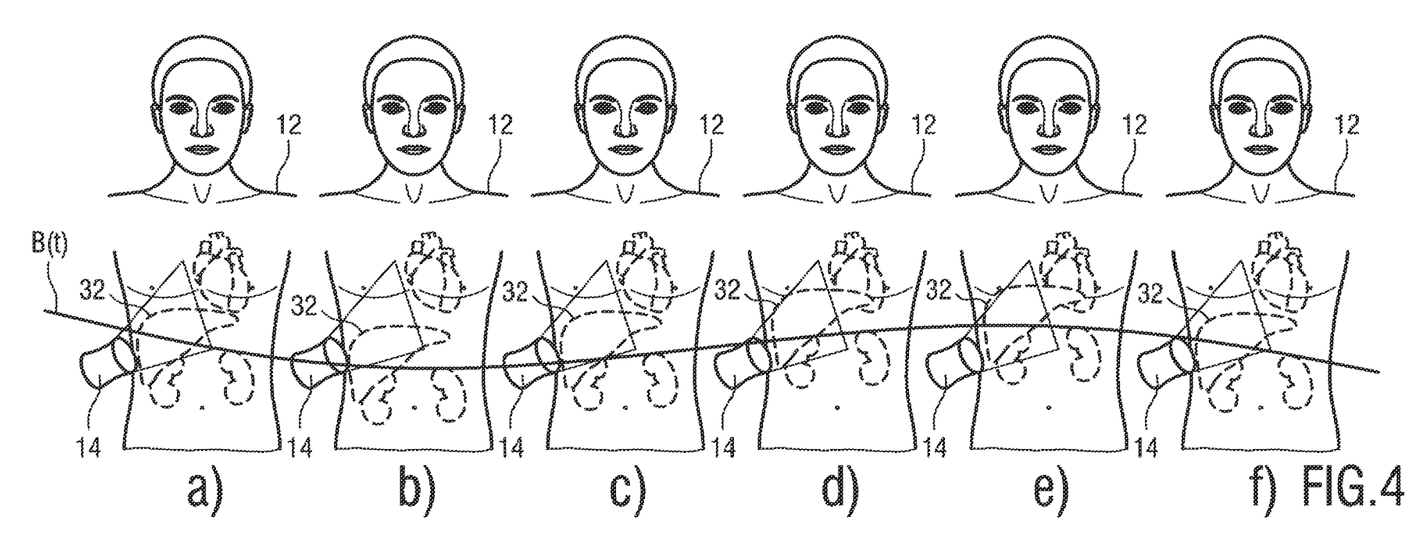
FIGS. 4a-f show different positions of the liver dependent on the respiration of the subject.
Figure 5:
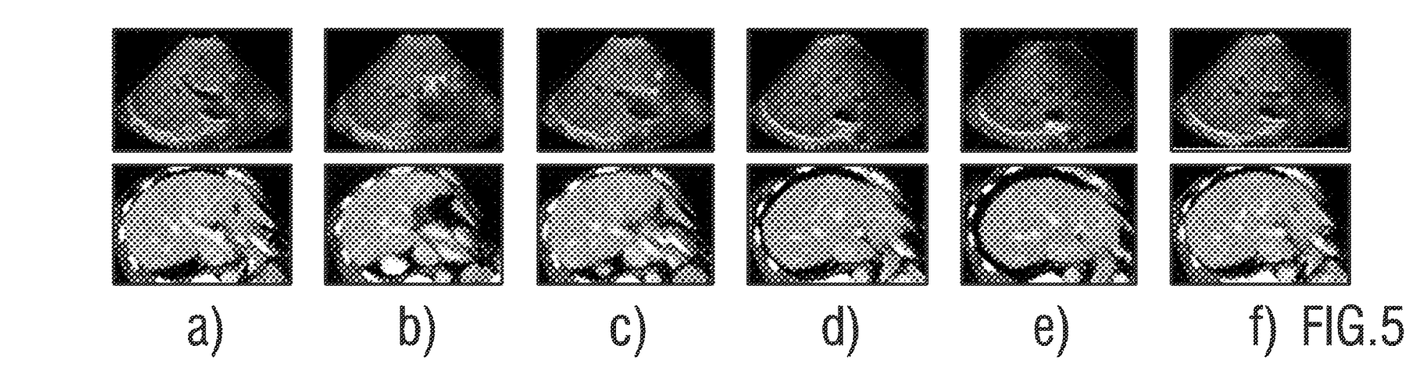
FIGS. 5a-f show ultrasound images and computer tomography images corresponding to the different positions of the liver of FIGS. 4a-f dependent on the respiration of the subject.

In FIGS. 4*a* and 5*a*, the calibration position is schematically shown, wherein the anatomical feature is in a medium or middle position as shown in FIG. 3. The anatomical feature, i.e. the liver 32 is as shown in FIG. 4*a* in a middle position, wherein the ultrasound image and the corresponding pre-operative computer tomography image are aligned or fused to each other as mentioned above. During exhale as shown in FIG. 4*b*, the liver 32 moves downwardly in the body of the subject 12 and, therefore, with respect to the ultrasound probe 14 so that a different ultrasound image is captured as shown in FIG. 5*b*. Based on the motion model of the anatomical feature 32, the new position of the liver 32 is determined and a different slice or image plane of the computer tomography image data is selected and registered with the amended ultrasound image as shown in FIG. 5*b*. At this fixed position an acquired plurality of ultrasound images (shown in FIG. 5 for example) shares a repetitive pattern of common anatomical features, based on a variation of this pattern with time the motion model for a given patient (for example, the model including a patient specific timing diagram such as in FIG. 3) can be determined. Correspondingly, the different positions of the liver 32 are determined within each ultrasound image of the plurality and the respective different slices or image planes of the computer tomography image data are selected for image correlation or fusion as shown in FIG. 5*c-f.*

Hence, the correct image plane of the computer tomography image data as the pre-operative medical image data can be selected during the respiration of the subject 12 so that a precise alignment of the different image data can be achieved.

Figure 6:
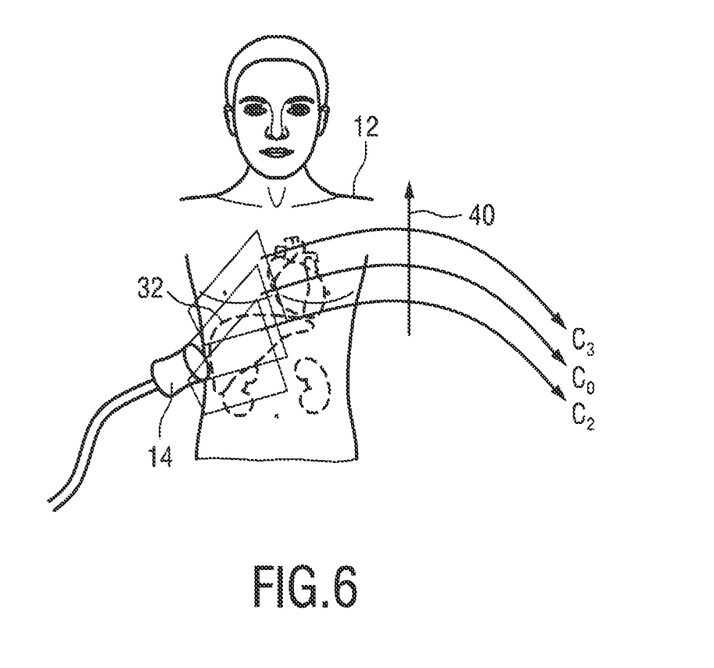
FIG. 6 shows a schematic diagram illustrating the selection of different image planes of the computer tomography data dependent on the respiration of the subject.

In FIG. 6 a schematic illustration of the subject 12 and different slices or image planes C of the pre-operative medical image data (e.g. computer tomography image data) is shown. During the fusion or registration of the ultrasound image data and the pre-operative medical image data, different slices or image planes C are defined in the pre-operative medical image data, wherein the slices or image planes C are parallel to each other and disposed or oriented in the direction of the motion or the cranio caudal direction.

The slices or image planes C for registration are selected among a set of slices or image planes C:

$$\{C_{-m}, \ldots, C_{-3}, C_{-2}, C_{-1}, C_0, C_1, C_2, \ldots, C_n\}$$

wherein $C_0$ is the slice or image plane C of the calibrated position or the initial position and the other slices or image planes are disposed in parallel to the calibrated slice or image plane $C_0$.

Dependent on the respiration of the subject 12, the liver 32 moves in the cranio-caudal direction 40, wherein one of the slices or image planes C of the pre-operative image data is selected based on the determined motion model 38.

The range in which the slices or image planes are provided is typically about a range of 21 mm. A typical amount of slices or image planes is 15 dependent on the sampling rate, wherein a large amount of slices or image planes C increases the complexity and computation effort and a reduced amount of slices or image planes reduces the complexity and accuracy.

The selection of the slices or image planes C can be based on a minimization criteria, wherein a distance between detected anatomical features in the ultrasound image data and the medical image data such as vessel is used, wherein a slice is selected having the lowest distances between the corresponding features. Other distances can be used such as mutual information or mean square error.

The selection may be based on the use of the dynamic programming such as Viterbi algorithm to an improved provide robustness of the selection. The purpose of the algorithm is to select the slice or image plane C not only on the distance criteria but also on the basis of a probability taking the respiration function B(t) into account.

In an alternative embodiment, the ultrasound probe 14 is a three-dimensional ultrasound probe, wherein the three-dimensional ultrasound image data is fused or registered with a corresponding pre-operative medical image data volume such as computer tomography data volume based on the respiration function B(t) and the motion model. The medical imaging apparatus 10 provides a corresponding set of medical image data volumes in the cranio-caudal direction 40, wherein the respective volume is selected based on the respiration function B(t) and the motion model.

Figure 7:
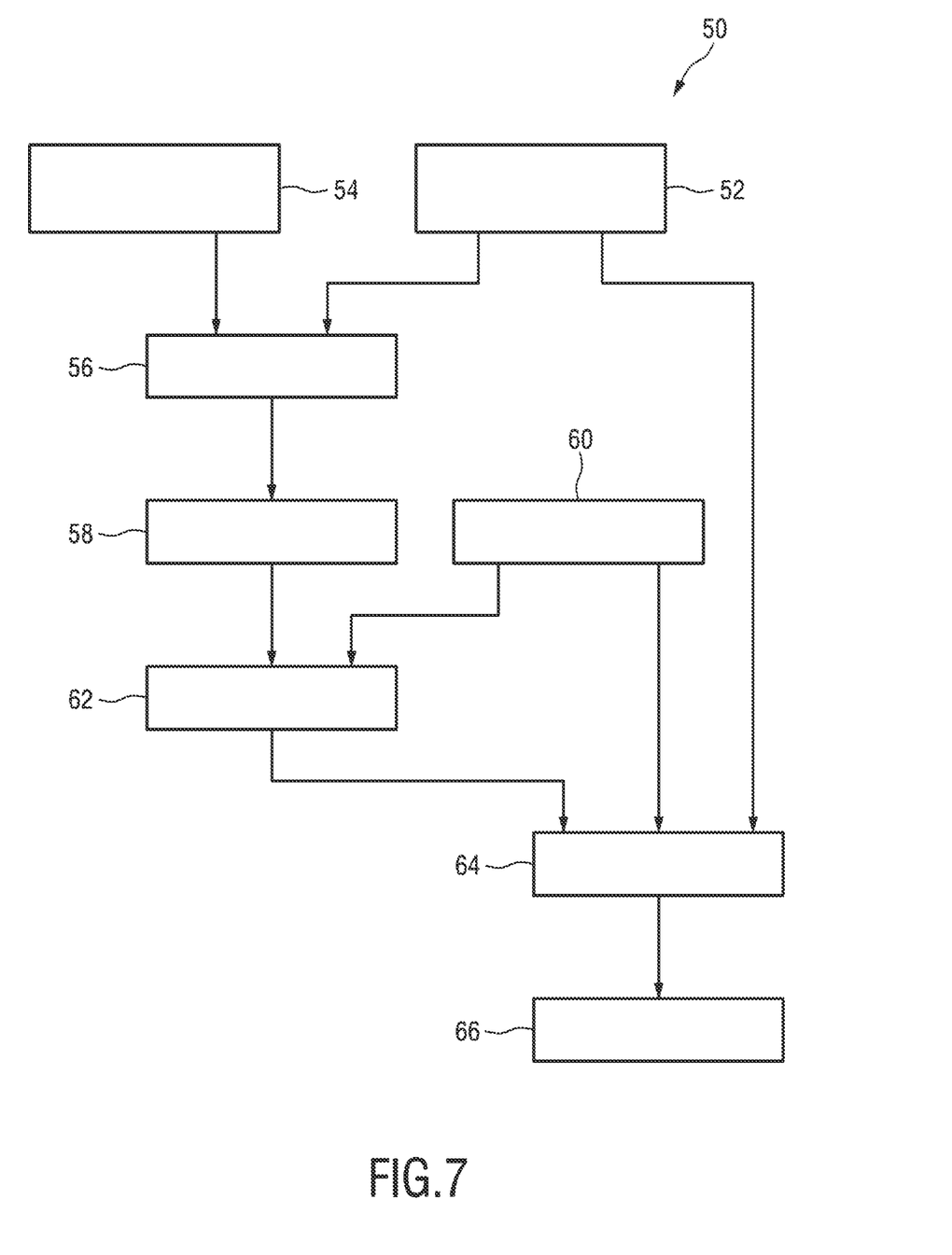
FIG. 7 shows a flow diagram of a medical imaging method for aligning ultrasound image data and preoperative medical image data of a subject.

FIG. 7 shows a schematic flow diagram of a medical imaging method for aligning ultrasound image data and preoperative medical image data of the subject 12. The medical imaging method is generally denoted by 50. The method 50 starts with providing three-dimensional medical image data such as computer tomography image data, magnet resonance tomography image data or the like as shown at 52. The position determining unit 30 provides a position of the ultrasound probe 14 as shown at 54. In step 56 the plurality of ultrasound images is acquired at the fixed position of the ultrasound probe 14. The image processing unit 18 via the alignment unit, for example, defines the motion model 38 based on the position of the ultrasound probe 14 and the variation of the repetitive pattern of the common anatomical features throughout the plurality of ultrasound images. It may be beneficial to define the motion model 38 based on at least one respiratory period of the respiration function B(t). This can provide a more precise motion model definition. At step 56 a motion state of the anatomical feature in the image data is determined based on the motion model 38, e.g. a respiratory state of the subject 12 so that a motion of the anatomical features of the subject and a following realignment can be estimated.

The fusion unit 24 determines based on the motion model 38 and the position of the ultrasound probe 14 a plurality of different image planes within the three-dimensional medical image as shown at step 58. The two-dimensionally ultrasound image data is continuously acquired at step 60 and one of the different image planes of the three-dimensional medical image data is selected at step 62, which fits best to the two-dimensional ultrasound image data acquired at step 60 in order to align the ultrasound image data and the three-dimensional medical image data. The image plane is selected e.g. based on pattern detection of corresponding anatomical features within the image planes of the three-dimensional image data and the ultrasound image data. After the alignment of the ultrasound image data to one of the image planes of the medical image data at step 62, the image data of the selected image plane and the ultrasound image data are fused to combined image data as shown at step 64 and displayed on the display screen 26 as shown at step 66.

Consequently, the ultrasound image data and the medical image data can be aligned continuously even if the anatomical features of the subject 12 to be imaged are in motion and precisely fused image data can be displayed on the display screen 26.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A medical imaging apparatus or inspecting a volume of a subject, comprising:
    an image interface for receiving a plurality of ultrasound image data acquired by an ultrasound probe, wherein the plurality of ultrasound image data is two dimensional data comprising a plurality of temporally discrete image planes, and medical image data of the subject, wherein the medical image data is three dimensional data comprising a plurality of image planes disposed parallel to one another and oriented in a cranio-caudal direction;
    a position determining unit for receiving a position data of the ultrasound probe; and
    an image processing unit configured to:
        determine a motion model of the volume based on the position of the ultrasound probe and a variation of a repetitive temporal pattern of anatomical features throughout the plurality of temporally discrete image planes, wherein the motion model includes a cranio-caudal translation model having a respiration function B(t) and is determined based on the plurality of ultrasound image data acquired during at least one respiratory period of the respiration function B(t);
        determine a motion state of the anatomical features in individual ones of the plurality of image planes of the medical image data based on the motion model;
        detect a pattern of the anatomical features in the medical image data and the plurality of ultrasound imaging data;
        select one of the plurality of image planes of the medical image data based on the pattern; and
        align the ultrasound image data and the one of the plurality of image planes of the medical image data based on the motion model,
    wherein the image processing unit comprises:
        a fusion unit for processing the ultrasound image data and the medical image data to fuse the ultrasound image data and the medical image data based on the alignment to combined image data.

2. The medical imaging apparatus as claimed in claim 1, wherein the image processing unit is adapted to determine corresponding anatomical features in the ultrasound data and the medical image data and to align the ultrasound data and the medical image data based on the corresponding anatomical features.

3. The medical imaging apparatus as claimed in claim 2, wherein the image processing unit is adapted to align the ultrasound data and the medical image data based on a distance between the determined corresponding anatomical features.

4. The medical imaging apparatus as claimed in claim 2, wherein the image processing unit is further configured to adapted the alignment of the ultrasound image data and the medical image data on the basis of the determined motion state.

5. The medical imaging apparatus as claimed in claim 1, wherein the image processing unit comprises a segmentation unit for providing segmentation data of anatomical features of the subject, and an alignment unit adapted to align the ultrasound image data and the medical image data based on the segmentation data.

6. The image medical imaging apparatus as claimed in claim 1, further comprising the ultrasound probe for acquiring the plurality of ultrasound image data, and wherein the position determining unit is arranged to determining a position of the ultrasound probe.

7. The medical imaging apparatus as claimed in claim 6, wherein the image processing unit is further configured to determine a subset of the plurality of image planes in the medical image data, based on the determined position of the ultrasound probe.

8. The medical imaging apparatus as claimed in claim 7, wherein the one of the plurality of image planes is selected from the subset of the plurality of image planes.

9. The medical imaging apparatus as claimed in claim 7, wherein the image processing unit is adapted to select one image plane of the subset of the plurality of image planes of the medical image data on the basis of a probability algorithm.

10. The medical imaging apparatus as claimed in claim 9, wherein the probability algorithm is a Viterbi algorithm.

11. The medical imaging apparatus as claimed in claim 1, wherein the motion model is determined based on the position of the ultrasound probe received from the position determining unit.

12. A medical imaging method for inspecting a volume of a subject, comprising the steps of:
    receiving a plurality of ultrasound image data acquired by an ultrasound probe, wherein the plurality of ultrasound image data is two dimensional data comprising a plurality of temporally discrete image planes;
    receiving medical image data of the subject via an image interface, wherein the medical image data is three dimensional data comprising a plurality of image planes disposed parallel to one another and oriented in a cranio-caudal direction;

receiving a position of the ultrasound probe;

determining a motion model of the volume based on the position of the ultrasound probe and a variation of a repetitive temporal pattern of anatomical features throughout the plurality temporally discrete image planes wherein the motion model includes a cranio-caudal translation model having a respiration function B(t) and is determined based on the plurality of ultrasound image data acquired during at least one respiratory period of the respiration function B(t);

determining a motion state of the anatomical features in individual ones of the plurality of image planes of the medical image data based on the motion model;

detecting a pattern of the anatomical features in the medical image data and the plurality of ultrasound imaging data;

selecting one of the plurality of image planes of the medical image data based on the pattern;

aligning the plurality of ultrasound image data and one of the plurality of image planes of the medical image data;

adapting the alignment of the plurality of ultrasound image data and one of the plurality of image planes of the medical image data based on the motion model; and processing the ultrasound image data and the medical image data to fuse the ultrasound image data and the medical image data based on the alignment to generate combined image data.

13. A non-transitory computer readable medium including instructions that when executed, cause an ultrasound imaging system to:

receive a plurality of ultrasound image data acquired by an ultrasound probe, wherein the plurality of ultrasound image data is two dimensional data comprising a plurality of temporally discrete image-planes;

receive medical image data of the subject via an image interface, wherein the medical image data is three dimensional data comprising a plurality of image planes disposed parallel to one another and oriented in a cranio-caudal direction;

receive a position of the ultrasound probe:

determine a motion model of the volume based on the position of the ultrasound probe and a variation of a repetitive temporal pattern of anatomical features throughout the plurality temporally discrete image planes wherein the motion model includes a cranio-caudal translation model having a respiration function B(t) and is determined based on the plurality of ultrasound image data acquired during at least one respiratory period of the respiration function B(t);

determine a motion state of the anatomical features in individual ones of the plurality of image planes of the medical image data based on the motion model;

detect a pattern of the anatomical features in the medical image data and the plurality of ultrasound imaging data;

select one of the plurality of image planes of the medical image data based on the pattern;

align the plurality of ultrasound image data and one of the plurality of image planes of the medical image data;

adapt the alignment of the plurality of ultrasound image data and one of the plurality of image planes of the medical image data based on the motion model; and process the ultrasound image data and the medical image data to fuse the ultrasound image data and the medical image data based on the alignment to generate combined image data.

\* \* \* \* \*